(12) United States Patent
Kanno

(10) Patent No.: US 10,749,244 B2
(45) Date of Patent: Aug. 18, 2020

(54) SUBSTRATE FOR MEDICAL DEVICE AND MEDICAL DEVICE

(71) Applicant: Sony Olympus Medical Solutions Inc., Tokyo (JP)

(72) Inventor: Kiyotaka Kanno, Saitama (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 507 days.

(21) Appl. No.: 15/516,850

(22) PCT Filed: Aug. 19, 2015

(86) PCT No.: PCT/JP2015/073255
§ 371 (c)(1),
(2) Date: Apr. 4, 2017

(87) PCT Pub. No.: WO2016/067716
PCT Pub. Date: May 6, 2016

(65) Prior Publication Data
US 2017/0294703 A1 Oct. 12, 2017

(30) Foreign Application Priority Data
Oct. 27, 2014 (JP) .................................. 2014-218673

(51) Int. Cl.
*H01Q 1/22* (2006.01)
*H04N 5/225* (2006.01)
(Continued)

(52) U.S. Cl.
CPC ....... *H01Q 1/2283* (2013.01); *A61B 1/00124* (2013.01); *A61B 1/04* (2013.01);
(Continued)

(58) Field of Classification Search
CPC ............ H01R 13/6471; A61B 1/00124; H04N 2005/2255; H01Q 1/2283; H01Q 21/28;
(Continued)

(56) References Cited

U.S. PATENT DOCUMENTS 4,853,772 A * 8/1989 Kikuchi ............... H04N 5/2251
348/71
5,390,662 A * 2/1995 Okada ..................... A61B 1/05
348/E5.026
(Continued)

FOREIGN PATENT DOCUMENTS

CN 103002788 A 3/2013
JP 11-221195 8/1999
(Continued)

OTHER PUBLICATIONS

International Search Report dated Oct. 13, 2015 in PCT/JP2015/073255 Filed Aug. 19, 2015.
(Continued)

*Primary Examiner* — John P Leubecker
*Assistant Examiner* — Shankar Raj Ghimire
(74) *Attorney, Agent, or Firm* — Xsensus LLP

(57) ABSTRACT

A substrate for a medical device, a portion of which is brought into contact with or inserted into a subject. The substrate includes a patient circuit conductively connected to the portion that is configured to be brought into contact with or inserted into the subject, and a ground-side circuit configured to perform at least one of transmission of a signal, reception of a signal, and supply of electric power on the patient circuit. The ground-side circuit is grounded by a protective ground to ensure safety of a manipulator of the medical device. The substrate also includes an insulating layer between the patient circuit and the ground-side circuit providing insulation between the patient circuit and the
(Continued)

ground-side circuit, and an isolated circuit provided apart from the patient circuit and the ground-side circuit on the insulating layer and having a different reference potential from the patient circuit and the ground-side circuit.

24 Claims, 5 Drawing Sheets

(51) Int. Cl.
| | |
|---|---|
| A61B 1/00 | (2006.01) |
| A61B 1/04 | (2006.01) |
| G02B 23/24 | (2006.01) |
| A61N 1/372 | (2006.01) |
| H01Q 21/28 | (2006.01) |
| H05K 1/18 | (2006.01) |
| H05K 1/02 | (2006.01) |

(52) U.S. Cl.
CPC ......... *A61N 1/37229* (2013.01); *G02B 23/24* (2013.01); *H01Q 21/28* (2013.01); *H04N 5/225* (2013.01); *H05K 1/0215* (2013.01); *H05K 1/185* (2013.01); *H05K 2201/0776* (2013.01)

(58) Field of Classification Search
CPC ...... G02B 23/24; H05K 1/0215; H05K 1/185; H05K 2201/0776
USPC .......................................................... 600/134
See application file for complete search history.

(56) References Cited

U.S. PATENT DOCUMENTS

| | | | | |
|---|---|---|---|---|
| 5,543,831 | A * | 8/1996 | Tsuji .................. | H04N 7/183 |
| | | | | 128/901 |
| 5,941,817 | A * | 8/1999 | Crawford .......... | A61B 1/00071 |
| | | | | 600/109 |
| 8,199,187 | B2 * | 6/2012 | Knapp, II .......... | A61B 1/00103 |
| | | | | 348/231.3 |
| 10,492,664 | B2 * | 12/2019 | Narita ................ | A61B 1/00124 |
| 2005/0064732 | A1 * | 3/2005 | Muench .............. | H01L 23/057 |
| | | | | 439/55 |
| 2007/0120751 | A1 * | 5/2007 | Saito .................. | H01Q 1/2283 |
| | | | | 343/702 |
| 2009/0105540 | A1 * | 4/2009 | Kawata .............. | A61B 1/00006 |
| | | | | 600/118 |
| 2012/0081861 | A1 * | 4/2012 | Shimada ............. | H05K 1/0228 |
| | | | | 361/737 |
| 2013/0150668 | A1 * | 6/2013 | Kanno ............... | A61B 1/00059 |
| | | | | 600/109 |
| 2013/0231870 | A1 * | 9/2013 | Sugnet ............... | G16B 40/00 |
| | | | | 702/19 |
| 2014/0301047 | A1 * | 10/2014 | Kato .................. | H05K 1/028 |
| | | | | 361/749 |
| 2014/0371530 | A1 * | 12/2014 | Wieters .............. | A61B 1/0011 |
| | | | | 600/109 |
| 2015/0224326 | A1 * | 8/2015 | Toth .................. | A61B 5/042 |
| | | | | 600/301 |
| 2015/0250378 | A1 * | 9/2015 | Tomatsu ............ | A61B 1/00124 |
| | | | | 348/75 |
| 2016/0099738 | A1 * | 4/2016 | Kodama ............. | H05K 1/147 |
| | | | | 455/575.6 |
| 2017/0012593 | A1 * | 1/2017 | Tanimizu ............ | H01F 27/022 |

FOREIGN PATENT DOCUMENTS

| | | | | |
|---|---|---|---|---|
| JP | 2000-279381 A | 10/2000 | | |
| JP | 2000-342531 | 12/2000 | | |
| JP | 2006-158598 | 6/2006 | | |
| JP | 2006-196608 | 7/2006 | | |
| JP | 2007-54150 | 3/2007 | | |
| JP | 2007-229305 A | 9/2007 | | |
| JP | 2010-19554 | 1/2010 | | |
| JP | 2012/005196 A1 | 1/2012 | | |
| JP | 2013074075 A * | 4/2013 | .......... | H01L 23/528 |
| JP | 2014-188210 A | 10/2014 | | |
| WO | WO-2016117373 A1 * | 7/2016 | ............... | A61B 1/04 |

OTHER PUBLICATIONS

Combined Chinese Office Action and Search Report dated Jun. 28, 2018 in corresponding Patent Application No. 201580056711.3 (with English Translation), citing document AO therein, 11 pages.

* cited by examiner

SUBSTRATE FOR MEDICAL DEVICE AND MEDICAL DEVICE

TECHNICAL FIELD

The present disclosure relates to a substrate for a medical device that is included in a medical device at least part of which is brought into contact with or inserted into a subject such as a person and a medical device.

BACKGROUND ART

Thus far, as medical devices at least part of which is brought into contact with or inserted into a subject such as a person, an endoscope system that observes the subject, an ultrasonic observation system including an ultrasonic endoscope system using ultrasonic waves, a treatment device system that applies energy to the subject, etc. have been commonly known. The medical device generally includes a patient circuit that is a circuit on the side of being brought into contact with or inserted into the subject and a ground-side circuit that is a circuit provided on the side of performing the transmission and reception of signals, the supply of electric power, etc. with the patient circuit and grounded by functional grounding, protective grounding for ensuring the safety of the manipulator of the medical device, or the like, such as the primary circuit and the secondary circuit. In such a medical device, electrical insulation is provided between the patient circuit and the ground-side circuit in order to ensure safety.

For the medical device, there is known a technology in which the reference potential of the patient circuit (the patient ground) and the reference potential of the ground-side circuit are connected by an impedance element such as a capacitor in an alternating current manner, and thereby the reference potential of the patient circuit is stabilized and the noise between the patient circuit and the ground-side circuit is reduced (e.g. see Patent Literature 1).

CITATION LIST

Patent Literature

Patent Literature 1: JP 2000-279381A

DISCLOSURE OF INVENTION

Technical Problem

In the case where, in a substrate for a medical device that includes the patient circuit and the ground-side circuit described above and in which the patient circuit and the ground-side circuit are connected by an impedance element, a capacitor is used as the impedance element, a capacitor of a dual inline package (DIP) type is generally used. However, in the patient circuit and the ground-side circuit of recent years, the proportion of, for example, electronic components of what is called a chip type such as a surface-mount device (SMD) type is large, and consequently a mounting process other than that for the chip-type electronic components has been needed in order to mount the DIP-type capacitor on the same substrate.

To solve the problem, it may be possible to use a chip-type ceramic capacitor as the impedance element. However, although a desired breakdown voltage capacity can be provided, a single-body large-sized ceramic capacitor by which the patient circuit and the ground-side circuit can be connected while a creeping distance of, for example, approximately 8 mm is ensured as the insulation distance between the patient circuit and the ground-side circuit may experience the cracking of the ceramic or the like, and the manufacturing has been technically difficult.

The present disclosure has been made in view of the above, and an object of the present disclosure is to provide a substrate for a medical device and a medical device in which the reference potential of the patient circuit can be stabilized, the noise between the patient circuit and the ground-side circuit can be reduced, and the insulation distance between the patient circuit and the ground-side circuit can be sufficiently ensured without using a large-sized electronic component.

Solution to Problem

In order to solve the above problem and achieve the object, a substrate for a medical device according to the present disclosure is configured to be included in a medical device at least part of which is brought into contact with or inserted into a subject, the substrate for a medical device including: a patient circuit that is a circuit on a side of being brought into contact with or inserted into the subject; a ground-side circuit that is a circuit configured to perform at least one of transmission of a signal, reception of a signal, and supply of electric power on the patient circuit and grounded; an insulating layer provided between the patient circuit and the ground-side circuit and providing insulation between the patient circuit and the ground-side circuit; and an isolated circuit provided apart from the patient circuit and the ground-side circuit on the insulating layer and having a different reference potential from the patient circuit and the ground-side circuit.

The substrate for a medical device according to the present disclosure, in the above invention, may further include a plurality of impedance means for connecting either one of the patient circuit and the ground-side circuit and the isolated circuit. The patient circuit and the ground-side circuit may be connected via the isolated circuit and at least part of the plurality of impedance means.

In the substrate for a medical device according to the present disclosure, in the above invention, the isolated circuit and the impedance means may be located on at least one of a first surface and a second surface that are surfaces in a thickness direction of the substrate for a medical device and an inner layer.

The substrate for a medical device according to the present disclosure, in the above invention, may further include: a plurality of the isolated circuits; and an impedance means for connecting two of the plurality of isolated circuits.

In the substrate for a medical device according to the present disclosure, in the above invention, the impedance means may be formed of a chip-type electronic component.

In the substrate for a medical device according to the present disclosure, in the above invention, the impedance means may be located on at least two of a first surface and a second surface that are surfaces in a thickness direction of the substrate for a medical device and an inner layer, and may be provided such that at least part of the impedance means overlap along the thickness direction of the substrate for a medical device.

The substrate for a medical device according to the present disclosure, in the above invention, may include a conduction fixing portion provided in the ground-side circuit and fixed in the medical device while being connected with conduction to a ground-side circuit or a grounding unit provided in the medical device and yet outside the substrate for a medical device.

A medical device according to the present disclosure, at least part of which is brought into contact with or inserted into a subject, includes a substrate for a medical device. The substrate for a medical device includes a patient circuit that is a circuit on a side of being brought into contact with or inserted into the subject, a ground-side circuit that is a circuit configured to perform at least one of transmission of a signal, reception of a signal, and supply of electric power on the patient circuit and grounded, an insulating layer provided between the patient circuit and the ground-side circuit and providing insulation between the patient circuit and the ground-side circuit, and an isolated circuit provided apart from the patient circuit and the ground-side circuit on the insulating layer and having a different reference potential from the patient circuit and the ground-side circuit.

The medical device according to the present disclosure, in the above invention, may include: a tip device including a circuit unit connected with conduction to the patient circuit and being configured to be brought into contact with or inserted into the subject; and a control device including the substrate for a medical device and being configured to control operation of the tip device.

The medical device according to the present disclosure, in the above invention, may further include an electrically conductive fixing means for fixing the substrate for a medical device in the medical device. The ground-side circuit may be grounded via the fixing means.

Advantageous Effects of Invention

According to the present disclosure, an isolated circuit that is provided away from the patient circuit and the ground-side circuit on the insulating layer between the patient circuit and the ground-side circuit and has a different reference potential from the patient circuit and the ground-side circuit is included; therefore, the reference potential of the patient circuit can be stabilized, the noise between the patient circuit and the ground-side circuit can be reduced, and the insulation distance between the patient circuit and the ground-side circuit can be sufficiently ensured without using a large-sized electronic component.

MODE(S) FOR CARRYING OUT THE INVENTION

Figure 1:
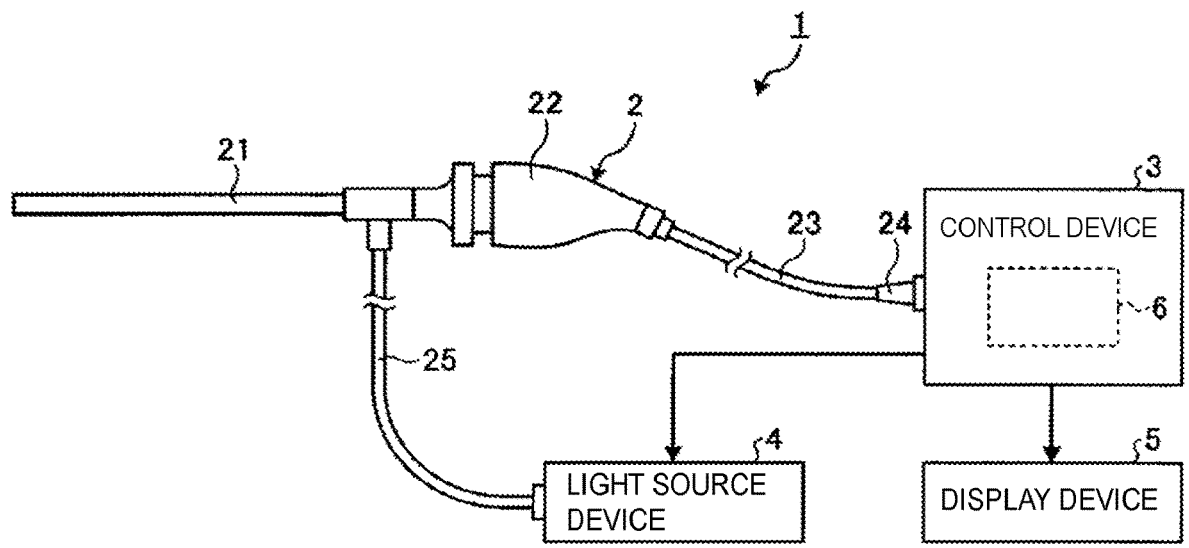
FIG. 1 is a diagram showing a rough configuration of an endoscope system that is a medical device according to an embodiment of the present disclosure.

Hereinbelow, embodiments of the present disclosure (hereinafter, referred to as "embodiments") are described with reference to the appended drawings. The drawings are only schematic ones, and portions for which the relationships between dimensions and the proportions are different among drawings may be included in the drawings.

FIG. 1 is a diagram showing a rough configuration of an endoscope system that is a medical device according to an embodiment of the present disclosure. An endoscope system 1 shown in the drawing is a device that observes the interior of a subject such as a person. The endoscope system 1 includes an endoscope 2 that captures an image of the interior of the subject by inserting its tip into the interior of the subject, a control device 3 that performs a prescribed image processing on an image of the interior of a body captured by the endoscope 2 to create image data for display and comprehensively controls the operation of the entire endoscope system 1, a light source device 4 that generates illumination light that is applied to the subject from the tip of the endoscope 2, and a display device 5 that includes a liquid crystal display panel or an organic electro-luminescence (EL) display panel and displays an image.

The endoscope 2 includes an insertion unit 21 that is rigid and has a long, thin shape and of which the tip is inserted into the interior of the subject, a camera head 22 that is connected to the root end of the insertion unit 21 in an attachable and detachable manner, and captures an image of the subject optically collected via the insertion unit 21 and outputs an imaging signal, a transmission cable 23 that transmits an imaging signal outputted by the camera head 22 to the control device 3, a connector 24 that is provided at the root end of the transmission cable 23 and is mounted on the control device 3 in an attachable and detachable manner, and a light guide 25 that transmits the illumination light generated by the light source device 4 to the tip of the insertion unit 21.

The insertion unit 21 includes a light collection optical system that is provided inside an outer casing having a cylindrical shape and collects light from the subject and an illumination optical system that is provided inside the outer casing and applies the illumination light transmitted from the light source device 4 via the light guide 25 to the subject. The light collection optical system and the illumination optical system are each configured using one or a plurality of lenses.

The camera head 22 includes an imaging element that photoelectrically converts the light collected by the optical system of the insertion unit 21 to generate an imaging signal and an input unit that accepts the input of an operation instruction signal of the endoscope 2. The imaging element is configured using an image sensor such as a charge-coupled device (CCD) or a complementary metal oxide semiconductor (CMOS).

The endoscope 2 having the above configuration includes a circuit unit connected with conduction to a patient circuit 7 included in a substrate for a medical device 6 described later, and has a function as a tip device that acquires the information of the subject.

Although the case where the endoscope 2 is a rigid endoscope is described in the embodiment, the present disclosure can be applied also to an endoscope system including a flexible endoscope or an ultrasonic endoscope, as a matter of course.

The control device 3 is a camera control unit that performs a prescribed signal processing on an imaging signal generated by the endoscope 2 to create image data of the subject. The control device 3 is configured using a central processing unit (CPU) etc.

The control device 3 includes a substrate for a medical device (hereinafter, simply referred to as a substrate) 6 that includes a patient circuit connected with conduction to the circuit unit of the endoscope 2 and a ground-side circuit that is a circuit that is grounded while being insulated from the patient circuit. The ground-side circuit is, for example, a circuit grounded by functional grounding, protective grounding for ensuring the safety of the manipulator of the endoscope system 1, or the like. More specifically, the ground-side circuit is, for example, the primary circuit that is grounded while being connected to a commercial power source and the secondary circuit insulated from the primary circuit.

Although the case where the control device 3 is a camera control unit is described in the embodiment, the present disclosure can be applied to any medical device for an endoscope system including a patient circuit and a ground-side circuit, such as a light source device that supplies illumination light to the endoscope 2 or a fluid supply device that supplies a fluid such as a gas or a liquid to the endoscope 2, as a matter of course. Further, although the case where the endoscope 2 and the control device 3 are separate devices is described in the embodiment, the present disclosure can be applied also to an endoscope device in which they are integrally provided, as a matter of course.

The configuration of the substrate 6 will now be described with reference to the plan view shown in FIG. 2. The substrate 6 shown in FIG. 2 includes a patient circuit 7, three ground-side circuits 8a, 8b, and 8c, and insulating layers 9a, 9b, and 9c formed between the patient circuit 7 and the ground-side circuits 8a, 8b, and 8c, respectively, and the major surface of the substrate 6 has a rectangular shape.

The patient circuit 7 is located in a central portion of the substrate 6, and has a T-shaped configuration. In FIG. 2, the patient circuit 7 is in a state of being laid horizontally, with the upper side of the T shape located on the right side of the drawing. The ground-side circuits 8a and 8b in a rectangular shape are provided on both sides of the vertical line of the T shape of the patient circuit 7 (in FIG. 2, above and below the vertical line of the T shape), respectively. The ground-side circuit 8c in a rectangular shape that has a long side equal in length to the horizontal line of the T shape is provided in a position facing the horizontal line of the T shape of the patient circuit 7 (in FIG. 2, on the right side of the horizontal line of the T shape). Thus, any one of the ground-side circuits 8a, 8b, and 8c is located in each of the four corners (end portions) of the substrate 6. By placing the three ground-side circuits 8a, 8b, and 8c in end portions of the substrate 6, the reference potential of the patient circuit 7 (the patient ground) can be stabilized.

The vicinities of, among the vertices of the ground-side circuits 8a and 8b, the vertices not connected to either of the insulating layers 9a and 9b have conduction fixing portions that are regions where holes 81a and 81b through which a fixing screw that is a fixing means for fixing the substrate 6 to the casing of the control device 3 is inserted are formed, respectively. Also the vicinities of, among the vertices of the ground-side circuit 8c, the two vertices not connected to the insulating layer 9c have conduction fixing portions that are regions where holes 81c and 82c through which a fixing screw is inserted are formed, respectively. The ground-side circuits 8a, 8b, and 8c are protectively grounded via the fixing screw and the casing.

The major surface of the insulating layer 9a has a hook-like shape. On the surface of the insulating layer 9a, an isolated circuit 31 that has a major surface having a rectangular shape and has a different reference potential from the patient circuit 7 and the ground-side circuit 8a is provided in a position apart from both of the patient circuit 7 and the ground-side circuit 8a. The isolated circuit 31 has at least a conduction pattern, and has a configuration in which an impedance element 51 described below and other various electronic components can be mounted as necessary.

The patient circuit 7 and the isolated circuit 31 are connected via an impedance element 51. The ground-side circuit 8a and the isolated circuit 31 are connected via an impedance element 52. That is, the impedance elements 51 and 52 are connected in series via the isolated circuit 31.

The impedance elements 51 and 52 are formed of any of a capacitor, a coil, and a resistance, or an appropriate combination of them, and have a function as an impedance means. The impedance element 51 and the impedance element 52 do not need to have the same configuration.

The impedance elements 51 and 52 may be either the DIP type or the surface-mount type, and is preferably the surface-mount type because they can be mounted together with other surface-mount-type electronic components that constitute the patient circuit 7 and the ground-side circuits 8a, 8b, and 8c and the number of manufacturing steps can be reduced.

The impedance elements 51 and 52 preferably have a sufficient breakdown voltage capacity not to cause breakdown even when an abnormal voltage occurs and all the voltage is applied to either one.

Although an impedance element of a capacitor, a coil, or a resistance is used as the impedance means in the embodiment, the impedance element is not limited to them, and a dielectric sheet or the like may be used.

The isolated circuits described below have at least a circuit pattern similarly to the isolated circuit 31 described above. The impedance elements described below are formed of any of a capacitor, a coil, and a resistance, or an appropriate combination of them, and have a function as an impedance means, similarly to the impedance element 51 etc. described above. Further, the impedance elements described below have a similar breakdown voltage capacity to the impedance element 51 etc.

The major surface of the insulating layer 9b has a hook-like shape. On the surface of the insulating layer 9b, an isolated circuit 32 that has a major surface having a rectangular shape and has a different reference potential from the patient circuit 7 and the ground-side circuit 8b is provided in a position apart from both of the patient circuit 7 and the ground-side circuit 8b. The patient circuit 7 and the isolated circuit 32 are connected via an impedance element 53. The ground-side circuit 8b and the isolated circuit 32 are connected via an impedance element 54. That is, the impedance elements 53 and 54 are connected in series via the isolated circuit 32.

The major surface of the insulating layer 9c has a straight-lined band shape. On the surface of the insulating layer 9c, isolated circuits 33, 34, and 35 that have a major surface having a rectangular shape and have a different reference potential from the patient circuit 7 and the ground-side circuit 8c are provided in positions apart from the patient circuit 7 and the ground-side circuit 8c. The patient circuit 7 and the isolated circuit 33 are connected via an impedance element 55. The ground-side circuit 8c and the isolated circuit 33 are connected via an impedance element 56. The patient circuit 7 and the isolated circuit 34 are connected via an impedance element 57. The ground-side circuit 8c and the isolated circuit 34 are connected via an impedance element 58. The patient circuit 7 and the isolated circuit 35 are connected via an IC for isolation 59. The isolated circuit 35 and the ground-side circuit 8c are connected via an IC for isolation 60.

Figure 2:
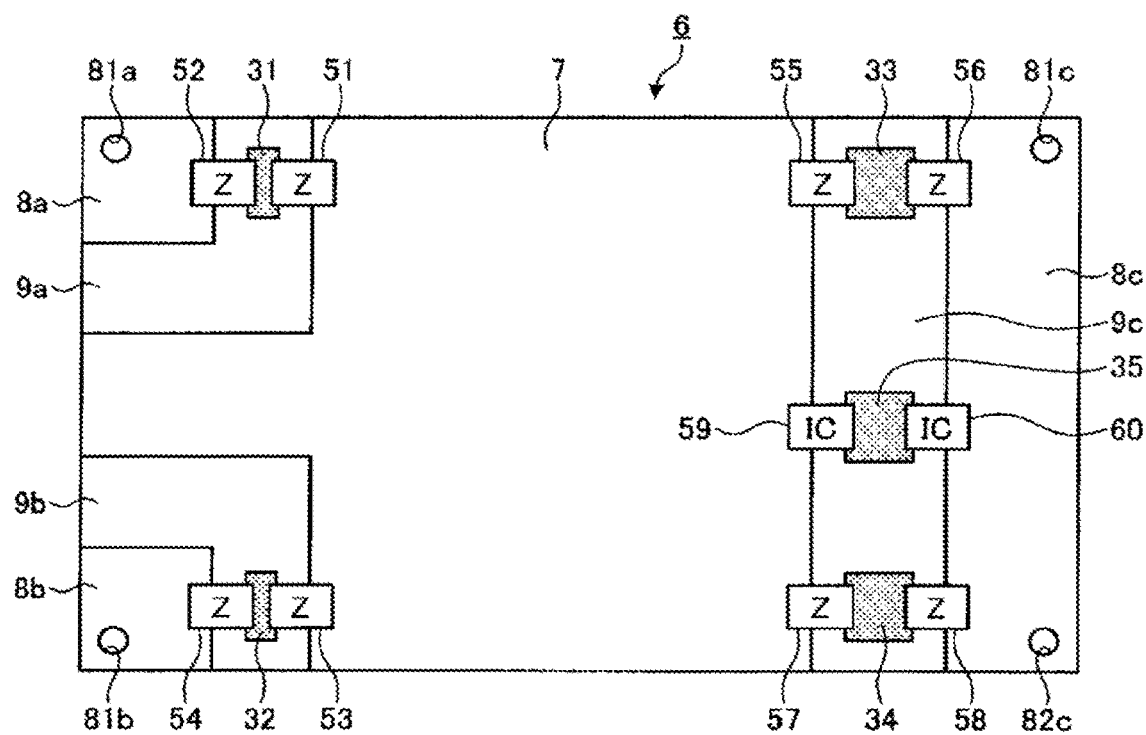
FIG. 2 is a plan view showing the configuration of a substrate for a medical device according to an embodiment of the present disclosure.

The impedance elements 51 to 58 are preferably placed in edge end portions of the substrate 6 as shown in FIG. 2. By placing the impedance elements 51 to 58 in edge end portions of the substrate 6, the reference potential of the patient circuit 7 can be stabilized more.

The substrate 6 having the above configuration may be a rigid substrate, a flexible substrate, or a rigid-flexible substrate.

In an embodiment of the present disclosure described above, an isolated circuit that is provided away from the patient circuit and the ground-side circuit and has a different reference potential from the patient circuit and the ground-side circuit is provided on the surface of the insulating layer between the patient circuit and the ground-side circuit, a plurality of impedance means for connecting either of the patient circuit and the ground-side circuit and the isolated circuit are provided, and the patient circuit and the ground-side circuit are connected via the isolated circuit and at least part of the plurality of impedance means; therefore, the patient circuit and the ground-side circuit can be linked even in a case where an impedance means alone could not link the patient circuit and the ground-side circuit, and there is no need to increase the size of the impedance means. Thus, by the embodiment, the reference potential of the patient circuit can be stabilized, the noise between the patient circuit and the ground-side circuit can be reduced, and the insulation distance between the patient circuit and the ground-side circuit can be sufficiently ensured without using a large-sized electronic component.

Furthermore, in the embodiment, since the impedance means is provided in an edge end portion of the substrate, the reference potential of the patient circuit can be considerably stabilized.

The shape of the major surface of the isolated circuit may be a shape other than a rectangular shape, such as a polygonal shape, a circular shape, or an elliptical shape. Further, the shape of the major surface of the isolated circuit may have a wavelike shape, or may have a shape in which the width changes on the way.

Although the case where the substrate 6 is provided in the control device 3 is described in the embodiment, the present disclosure can be applied also to the case where the substrate 6 is provided in the endoscope 2, as a matter of course.

Modification Example 1

Figure 3:
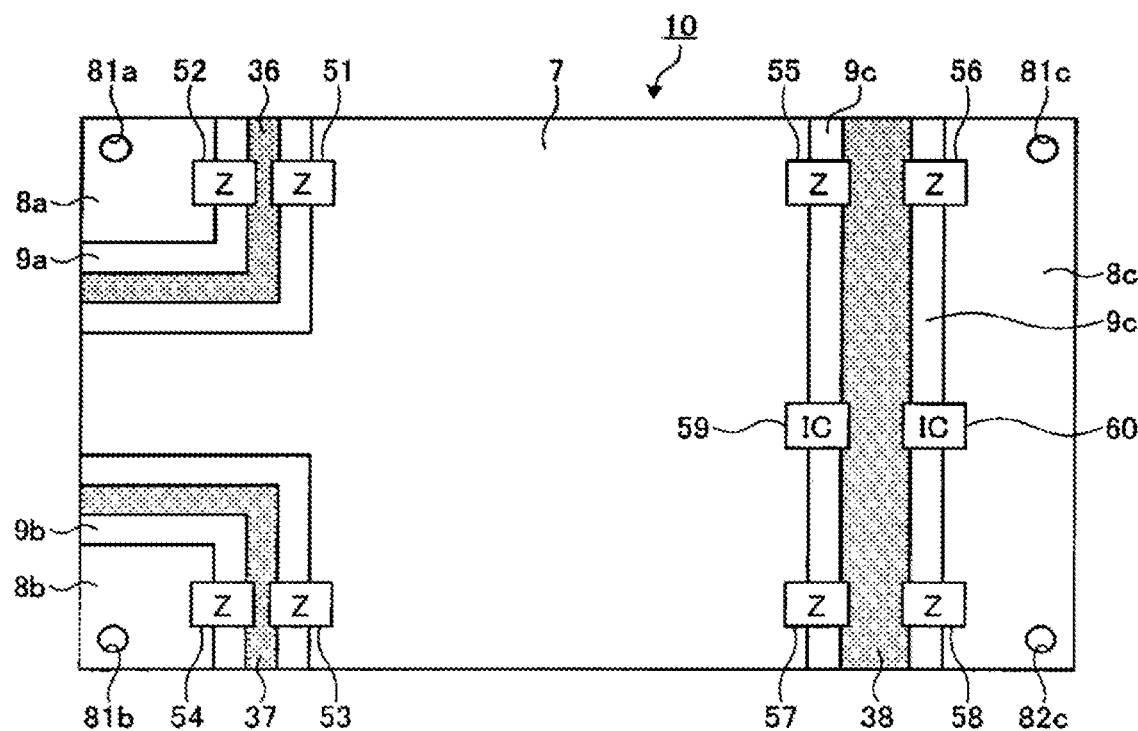
FIG. 3 is a plan view showing the configuration of a substrate for a medical device according to Modification Example 1 of an embodiment of the present disclosure.

FIG. 3 is a plan view showing the configuration of a substrate according to Modification Example 1 of the embodiment. A substrate 10 shown in the drawing differs from the substrate 6 described in Embodiment 1 in the configuration of the isolated circuit. The configuration of the isolated circuit of the substrate 10 will now be described.

On the surface of the insulating layer 9a, an isolated circuit 36 that is formed so as to connect two mutually orthogonal sides of the substrate 10 while running along the center in the width direction of the insulating layer 9a, which has a major surface having a hook-like shape, and has a major surface having a hook-like shape is provided. The patient circuit 7 and the isolated circuit 36 are connected via the impedance element 51. The ground-side circuit 8a and the isolated circuit 36 are connected via the impedance element 52.

On the surface of the insulating layer 9b, an isolated circuit 37 that is formed so as to connect two mutually orthogonal sides of the substrate 10 while running along the center in the width direction of the insulating layer 9b, which has a major surface having a hook-like shape, and has a major surface having a hook-like shape is provided. The patient circuit 7 and the isolated circuit 37 are connected via the impedance element 53. The ground-side circuit 8b and the isolated circuit 37 are connected via the impedance element 54.

On the surface of the insulating layer 9c, an isolated circuit 38 that is formed so as to connect two mutually facing sides of the substrate 10 while running along the center in the band width direction of the insulating layer 9c, which has a band shape, and has a straight-lined band shape is provided. The patient circuit 7 and the isolated circuit 38 are connected via the impedance elements 55 and 57 and the IC for isolation 59. The ground-side circuit 8c and the isolated circuit 38 are connected via the impedance elements 56 and 58 and the IC for isolation 60.

In Modification Example 1 of the embodiment described above, since the isolated circuit is formed so as to divide the major surface of the insulating layer into two parts, the flexibility of selection and placement of the impedance element can be enhanced.

Modification Example 2

Figure 4:
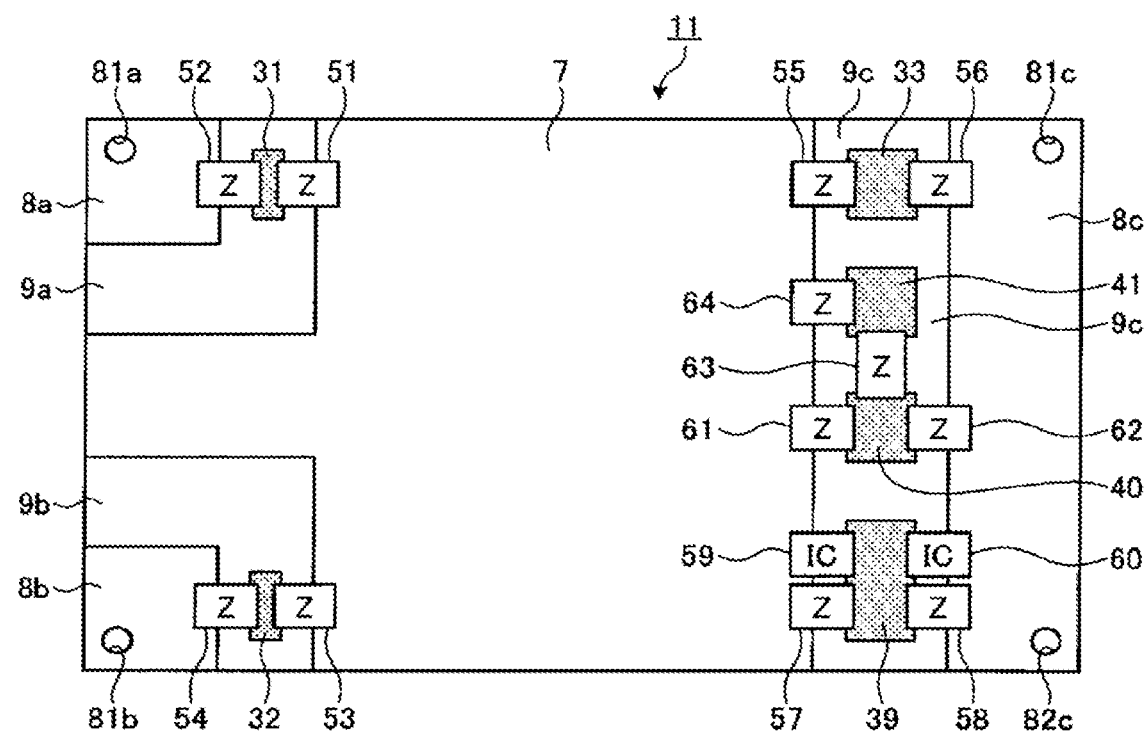
FIG. 4 is a plan view showing the configuration of a substrate for a medical device according to Modification Example 2 of an embodiment of the present disclosure.

FIG. 4 is a plan view showing the configuration of a substrate according to Modification Example 2 of the embodiment. A substrate 11 shown in the drawing differs from the substrate 6 described in Embodiment 1 in the configuration of the isolated circuit provided on the insulating layer 9c between the patient circuit 7 and the ground-side circuit 8c and the configuration of the impedance element connected to the isolated circuit. The configuration different from the substrate 6 out of the configuration of the substrate 11 will now be described.

On the surface of the insulating layer 9c, isolated circuits 39 to 41 are provided in addition to the isolated circuit 33. Of them, the isolated circuit 39 has a rectangular shape in which the longitudinal direction of the insulating layer 9c is taken as the long side direction, and the two impedance elements 57 and 58 and the two ICs for isolation 59 and 60 are connected to the isolated circuit 39. The patient circuit 7 and the isolated circuit 39 are connected via the impedance element 57 and the IC for isolation 59. The ground-side circuit 8c and the isolated circuit 39 are connected via the impedance element 58 and the IC for isolation 60.

The isolated circuit 40 is connected to the patient circuit 7 via an impedance element 61, and is connected to the ground-side circuit 8c via an impedance element 62. The isolated circuit 40 is connected to the isolated circuit 41 via an impedance element 63.

The isolated circuit 41 is connected to the patient circuit 7 via an impedance element 64.

In Modification Example 2 of the embodiment described above, the insulation distance between the patient circuit and the ground-side circuit can be made still longer by connecting different isolated circuits by means of impedance elements.

Modification Example 3

Figure 5:
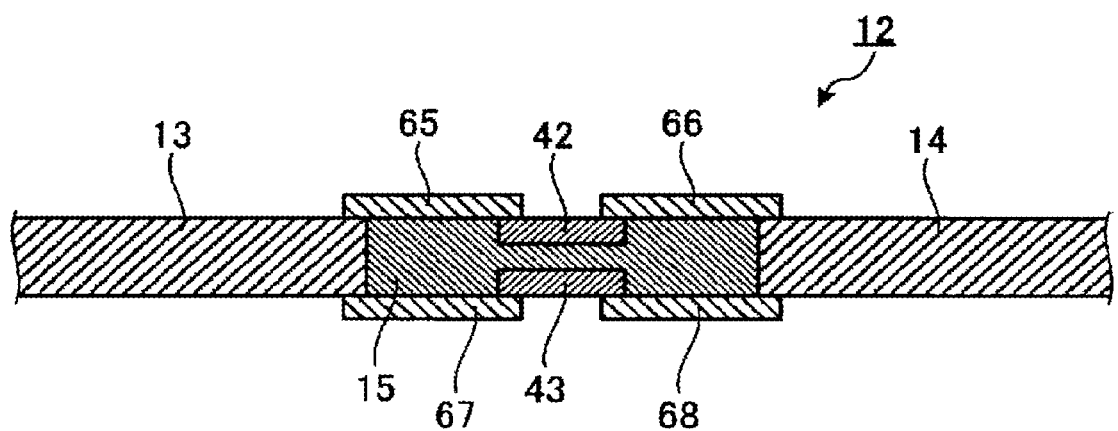
FIG. 5 is a cross-sectional view showing the configuration of a main part of a substrate for a medical device according to Modification Example 3 of an embodiment of the present disclosure.

FIG. 5 is a cross-sectional view showing the configuration of a main part of a substrate according to Modification Example 3 of the embodiment. A substrate 12 shown in the drawing includes a patient circuit 13, a ground-side circuit 14, and an insulating layer 15 provided between the patient circuit 13 and the ground-side circuit 14. On one surface of the insulating layer 15, an isolated circuit 42 is provided in a position apart from the patient circuit 13 and the ground-side circuit 14; on the other surface of the insulating layer 15, an isolated circuit 43 is provided in a position apart from the patient circuit 13 and the ground-side circuit 14.

The patient circuit 13 and the isolated circuit 42 are connected via an impedance element 65. The ground-side circuit 14 and the isolated circuit 42 are connected via an impedance element 66. The patient circuit 13 and the isolated circuit 43 are connected via an impedance element 67. The ground-side circuit 14 and the isolated circuit 43 are connected via an impedance element 68. The impedance elements 65 to 68 are surface-mount-type electronic components.

In Modification Example 3 of the embodiment described above, an isolated circuit is formed on both surfaces (a first and a second surface) in the thickness direction of the substrate, and the patient circuit and the ground-side circuit are connected on both surfaces using a surface-mount-type impedance element; therefore, the flexibility of selection and placement of the impedance element can be enhanced.

Furthermore, in the Modification Example 3, since a surface-mount-type impedance element is used, the number of manufacturing steps of the substrate can be made smaller than in the case of using a DIP-type impedance element.

It is also possible to employ a configuration in which one isolated circuit is provided so as to be exposed on both surfaces of the insulating layer and an impedance element is connected to the isolated circuit on both surface sides.

Modification Example 4

Figure 6:
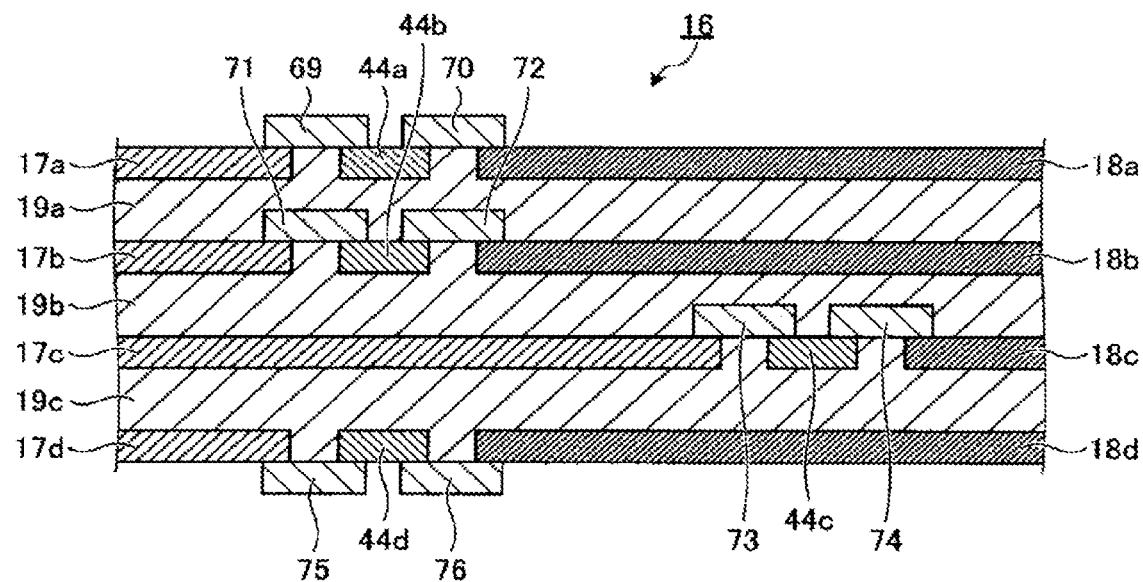
FIG. 6 is a cross-sectional view showing the configuration of a main part of a substrate for a medical device according to Modification Example 4 of an embodiment of the present disclosure.

FIG. 6 is a cross-sectional view showing the configuration of a main part of a substrate according to Modification Example 4 of the embodiment. A substrate 16 shown in the drawing includes patient circuits 17a, 17b, 17c, and 17d, ground-side circuits 18a, 18b, 18c, and 18d, insulating layers 19a, 19b, 19c, and 19d, and isolated circuits 44a, 44b, 44c, and 44d.

On the surface of the insulating layer 19a, the patient circuit 17a, the ground-side circuit 18a, and the isolated circuit 44a are provided apart from each other. The patient circuit 17a and the isolated circuit 44a are connected via an impedance element 69. The ground-side circuit 18a and the isolated circuit 44a are connected via an impedance element 70.

On the surface of the insulating layer 19b, the patient circuit 17b, the ground-side circuit 18b, and the isolated circuit 44b are provided apart from each other. The patient circuit 17b and the isolated circuit 44b are connected via an impedance element 71. The ground-side circuit 18b and the isolated circuit 44b are connected via an impedance element 72. The insulating layer 19a is stacked on the surfaces of the patient circuit 17b, the ground-side circuit 18b, the isolated circuit 44b, and the impedance elements 71 and 72. In other words, the patient circuit 17a, the ground-side circuit 18a, the isolated circuit 44a, and the impedance elements 69 and 70 are provided to be stacked on one surface of the insulating layer 19a, and the patient circuit 17b, the ground-side circuit 18b, the isolated circuit 44b, and the impedance elements 71 and 72 are provided to be stacked on the other surface of the insulating layer 19a.

On the surface of the insulating layer 19c, the patient circuit 17c, the ground-side circuit 18c, and the isolated circuit 44c are provided apart from each other. The patient circuit 17c and the isolated circuit 44c are connected via an impedance element 73. The ground-side circuit 18c and the isolated circuit 44c are connected via an impedance element 74. The insulating layer 19b is stacked on the surfaces of the patient circuit 17c, the ground-side circuit 18c, the isolated circuit 44c, and the impedance elements 73 and 74. In other words, the patient circuit 17b, the ground-side circuit 18b, the isolated circuit 44b, and the impedance elements 71 and 72 are provided to be stacked on one surface of the insulating layer 19b, and the patient circuit 17c, the ground-side circuit 18c, the isolated circuit 44c, and the impedance elements 73 and 74 are provided to be stacked on the other surface of the insulating layer 19b.

The impedance elements 69 and 70 are located on one surface (a first surface) of the substrate 16, and impedance elements 75 and 76 are located on the other surface (a second surface) of the substrate 16. The impedance elements 71 to 74 are located on the inner layer of the substrate 16. The impedance elements 69 to 75 are provided such that at least part of them overlap along the stacking direction of the substrate 16 (the thickness direction of the substrate 16).

In Modification Example 4 of the embodiment described above, an isolated circuit is formed on both surfaces and each inner layer of the substrate, and the patient circuit and the ground-side circuit are connected using a chip-type impedance element; therefore, an isolated circuit and an impedance element can be provided for each of a plurality of pairs of a patient circuit and a ground-side circuit efficiently, and the flexibility of placement of the patient circuit, the ground-side circuit, the isolated circuit, and the impedance element can be enhanced.

Furthermore, in the Modification Example 4, since a chip-type impedance element is used, there is no need to cause a connection terminal to penetrate through the substrate like in a DIP-type impedance element, and the impedance element can be located arbitrarily on at least any two of the first and second surfaces and the inner layer; therefore, the flexibility of placement of the impedance element can be enhanced.

In the Modification Example 4, the isolated circuit may be provided only on the necessary layer or surface.

Modification Example 5

Figure 7:
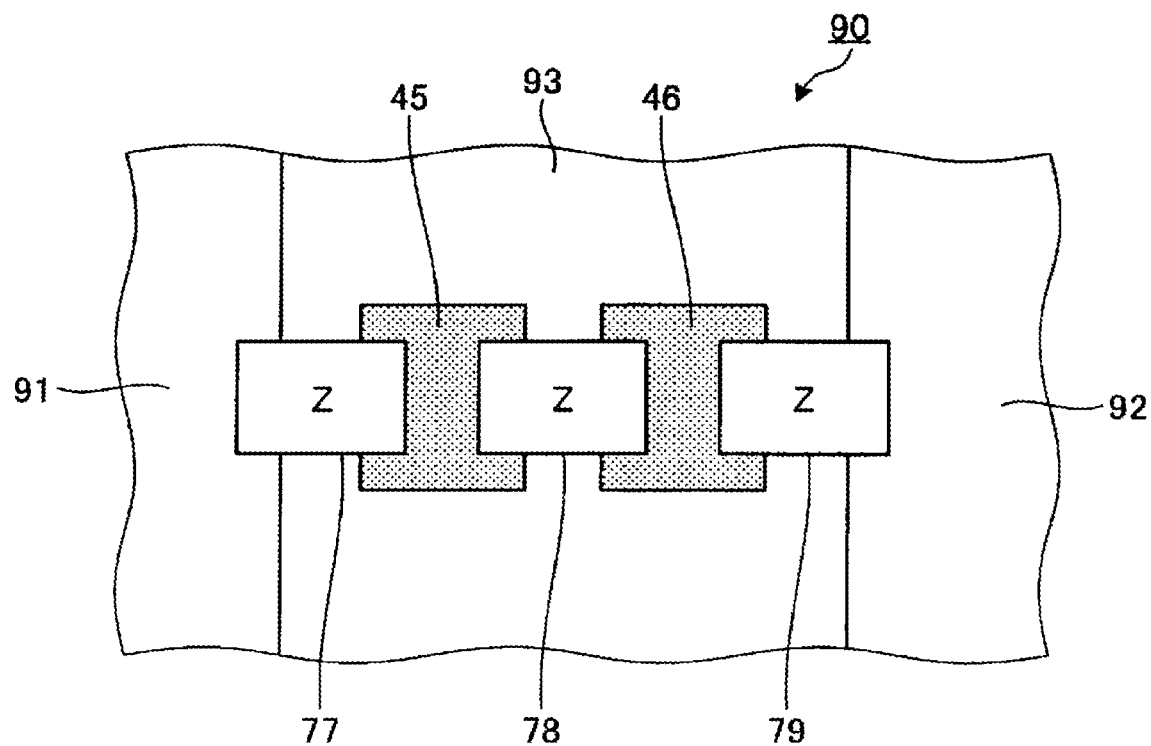
FIG. 7 is a plan view showing the configuration of a main part of a substrate for a medical device according to Modification Example 5 of an embodiment of the present disclosure.

FIG. 7 is a plan view showing the configuration of a main part of a substrate according to Modification Example 5 of the embodiment. A substrate 90 shown in the drawing includes a patient circuit 91, a ground-side circuit 92, and an insulating layer 93 provided between the patient circuit 91 and the ground-side circuit 92. On the surface of the insulating layer 93, two isolated circuits 45 and 46 are formed side by side in a state of being apart from each other along the width direction (the left and right direction of the drawing) and being apart from the patient circuit 91 and the ground-side circuit 92.

The isolated circuit 45 is connected to the patient circuit 91 via an impedance element 77. The isolated circuit 45 is connected to the isolated circuit 46 via an impedance element 78. The isolated circuit 46 is connected to the ground-side circuit 92 via an impedance element 79.

In Modification Example 5 of the embodiment described above, since the patient circuit and the ground-side circuit are connected using a plurality of isolated circuits and a plurality of impedance elements, there is no need to increase the size of the impedance element, and a plurality of small-sized impedance elements can be connected in series. Thus, the range of selection of the impedance element can be expanded.

The number of isolated circuits arranged in the width direction of the insulating layer may be altered in accordance with conditions such as the width of the insulating layer and the size of the impedance element as appropriate, and may be not less than the three described above.

Modification Example 6

Figure 8:
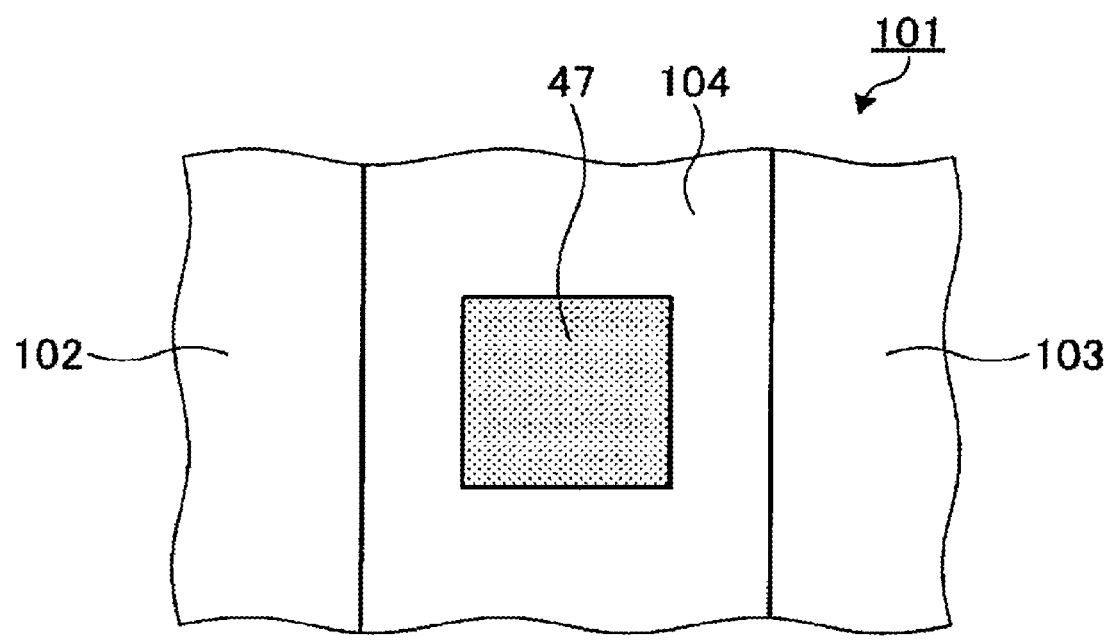
FIG. 8 is a plan view showing the configuration of a main part of a substrate for a medical device according to Modification Example 6 of an embodiment of the present disclosure.

FIG. 8 is a plan view showing the configuration of a main part of a substrate according to Modification Example 6 of the embodiment. A substrate 101 shown in the drawing includes a patient circuit 102, a ground-side circuit 103, and an insulating layer 104 provided between the patient circuit 102 and the ground-side circuit 103. On the surface of the insulating layer 104, an isolated circuit 47 is provided in a position apart from the patient circuit 102 and the ground-side circuit 103.

No impedance element is connected to the isolated circuit 47. Even in such a configuration, stray capacitance is present between the isolated circuit 47, and the patient circuit 102 and the ground-side circuit 103, and therefore similar effects to those in the case where the patient circuit 102 and the ground-side circuit 103 are connected using an impedance element can be obtained.

Other Embodiments

Hereinabove, embodiments of the present disclosure are described; but the present disclosure is not limited to the embodiments described above. For example, it is also possible to configure a substrate by combining the configurations described in the embodiment and Modification Examples 1 to 6 as appropriate.

Further, the shape and placement of the patient circuit and the ground-side circuit described in the embodiment and Modification Examples 1 and 2 are only examples, and other shapes and placements may be employed.

Further, although in the embodiments described above the substrate 6 etc. are described as one fixed to the control device 3, the substrate 6 etc. may be provided in the interior of the endoscope 2 or the light source device 4. Among these cases, in the case where the substrate 6 etc. are provided in the interior of the endoscope 2, it is preferable that the length of the portion of the patient circuit be shorter.

Further, other than the impedance element and the IC for isolation, a circuit for sequence control may be provided as a circuit element connected to the isolated circuit, for example.

The present disclosure can be applied to all kinds of medical devices that are brought into contact with or inserted into a subject and perform the observation, treatment, etc. of the subject. Examples of such a medical device include an ultrasonic diagnostic system using ultrasonic waves, a treatment equipment system that applies energy to a subject, an X-ray device using X-rays, etc. The present disclosure can be applied more generally to any medical device at least part of which can be brought into contact with or inserted into a subject such as a person and that includes a patient circuit and a ground-side circuit, regardless of whether it is for observation use or for treatment use.

Figure 9:
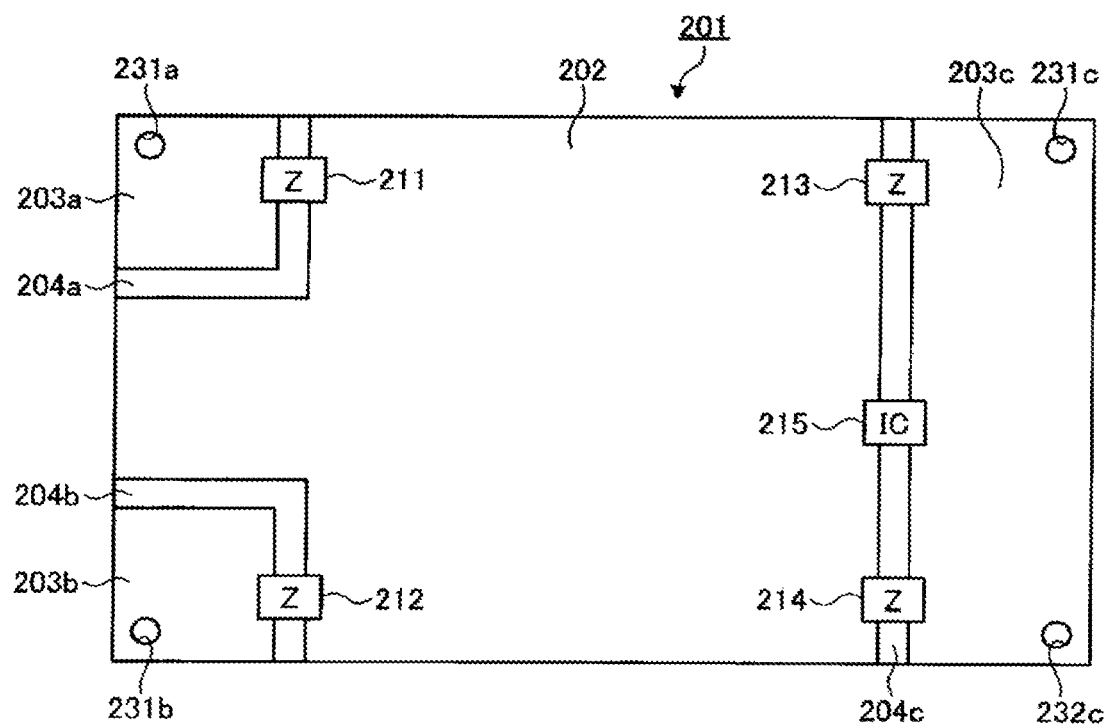
FIG. 9 is a plan view showing the configuration of a substrate for a medical device according to another embodiment.

FIG. 9 is a plan view showing the configuration of a substrate according to another embodiment. A substrate 201 shown in the drawing includes a patient circuit 202, three ground-side circuits 203a, 203b, and 203c, and insulating layers 204a, 204b, and 204c formed between the patient circuit 202 and the ground-side circuits 203a, 203b, and 203c, respectively. The major surface of the insulating layers 204a and 204b has a hook-like shape. The major surface of the insulating layer 204c has a straight-lined band shape.

The major surface of the substrate 201 has a rectangular shape, and the patient circuit 202 having a T-shaped configuration is provided in a central portion of the major surface. The ground-side circuits 203a and 203b having a rectangular shape are provided individually on both sides of the vertical line of the T shape of the patient circuit 202. The ground-side circuit 203c having a rectangular shape in which the long side is equal in length to the horizontal line of the T shape is provided in a position facing the horizontal line of the T shape of the patient circuit 202. Any one of the ground-side circuits 203a, 203b, and 203c is located in each of the four corners of the substrate 201.

In the vicinities of, among the vertices of the ground-side circuits 203a and 203b, the vertices not connected to either of the insulating layers 204a and 204b, holes 231a and 231b through which a fixing screw for fixing the substrate 201 to the casing of the control device included in the medical device is inserted are formed, respectively. Also in the vicinities of, among the vertices of the ground-side circuit 203c, the two vertices not connected to the insulating layer 204c, holes 231c and 232c through which a fixing screw is inserted are formed, respectively. The ground-side circuits 203a, 203b, and 203c are protectively grounded via the fixing screw and the casing.

The patient circuit 202 and the ground-side circuits 203a and 203b are connected via impedance elements 211 and 212, respectively. The patient circuit 202 and the ground-side circuit 203c are connected via impedance elements 213 and 214 and an IC for isolation 215.

The impedance elements 211 to 214 are located in edge end portions of the substrate 201. Therefore, the reference potential of the patient circuit 202 can be stabilized by the substrate 201.

Additionally, the present technology may also be configured as below.

(1)

A substrate for a medical device configured to be included in a medical device at least part of which is brought into contact with or inserted into a subject, the substrate for a medical device including:

a patient circuit that is a circuit on a side of being brought into contact with or inserted into the subject;

a ground-side circuit that is a circuit configured to perform at least one of transmission of a signal, reception of a signal, and supply of electric power on the patient circuit and grounded;

an insulating layer provided between the patient circuit and the ground-side circuit and providing insulation between the patient circuit and the ground-side circuit; and an isolated circuit provided apart from the patient circuit and the ground-side circuit on the insulating layer and having a different reference potential from the patient circuit and the ground-side circuit.

(2)

The substrate for a medical device according to (1), further including a plurality of impedance means for connecting either one of the patient circuit and the ground-side circuit and the isolated circuit, wherein the patient circuit and the ground-side circuit are connected via the isolated circuit and at least part of the plurality of impedance means.

(3)

The substrate for a medical device according to (2), wherein the isolated circuit and the impedance means are located on at least one of a first surface and a second surface that are surfaces in a thickness direction of the substrate for a medical device and an inner layer.

(4)

The substrate for a medical device according to any one of (1) to (3), further including:

a plurality of the isolated circuits; and an impedance means for connecting two of the plurality of isolated circuits.

(5)

The substrate for a medical device according to any one of (2) to (4), wherein the impedance means is formed of a chip-type electronic component.

(6)

The substrate for a medical device according to (5), wherein the impedance means is located on at least two of a first surface and a second surface that are surfaces in a thickness direction of the substrate for a medical device and an inner layer, and is provided such that at least part of the impedance means overlap along the thickness direction of the substrate for a medical device.

(7)

The substrate for a medical device according to any one of (1) to (6), including a conduction fixing portion provided in the ground-side circuit and fixed in the medical device while being connected with conduction to a ground-side circuit or a grounding unit provided in the medical device and yet outside the substrate for a medical device.

(8)

A medical device including the substrate for a medical device according to any one of (1) to (7).

(9)

The medical device according to (8), including:

a tip device including a circuit unit connected with conduction to the patient circuit and being configured to be brought into contact with or inserted into the subject; and a control device including the substrate for a medical device and being configured to control operation of the tip device.

(10)

The medical device according to (8) or (9), further including an electrically conductive fixing means for fixing the substrate for a medical device in the medical device, wherein the ground-side circuit is grounded via the fixing means.

REFERENCE SIGNS LIST 1 endoscope system
2 endoscope
3 control device
4 light source device
5 display device
6, 10, 11, 12, 16, 90, 101 substrate
7, 13, 17a, 17b, 17c, 17d, 91, 102 patient circuit
8a, 8b, 8c, 14, 18a, 18b, 18c, 18d, 92, 103 ground-side circuit
9a, 9b, 9c, 15, 19a, 19b, 19c, 19d, 93, 104 insulating layer
31 to 43, 44a, 44b, 44c, 44d, 45 to 47 isolated circuit
51 to 79 impedance element
59, 60 IC for isolation
81a, 81b, 81c, 82c hole

The invention claimed is:

1. A substrate for a medical device configured to be included in the medical device, a portion of which is brought into contact with or inserted into a subject,
the substrate for the medical device comprising:
a patient circuit that is conductively connected to the portion of the medical device that is configured to be brought into contact with or inserted into the subject;
a ground-side circuit that is a circuit configured to perform at least one of transmission of a signal, reception of a signal, and supply of electric power on the patient circuit, the ground-side circuit being grounded by a protective ground to ensure safety of a manipulator of the medical device;
an insulating layer provided between the patient circuit and the ground-side circuit and providing insulation between the patient circuit and the ground-side circuit;
an isolated circuit provided apart from the patient circuit and the ground-side circuit on the insulating layer and having a different reference potential from the patient circuit and the ground-side circuit; and
a first impedance circuit that connects the patient circuit to the isolated circuit, and a second impedance circuit that connects the ground-side circuit to the isolated circuit, at least one of the first and second impedance circuits being formed of a chip-type surface mount electronic component.

2. The substrate for the medical device according to claim 1, further comprising a plurality of impedance means for connecting either one of the patient circuit and the ground-side circuit and the isolated circuit,
wherein the patient circuit and the ground-side circuit are connected via the isolated circuit and at least part of the plurality of impedance means.

3. The substrate for the medical device according to claim 2, wherein the isolated circuit and the impedance means are located on at least one of a first surface and a second surface that are inner layers of surfaces in a thickness direction of the substrate for the medical device.

4. The substrate for the medical device according to claim 2, wherein the impedance means is formed of a chip-type electronic component.

5. The substrate for the medical device according to claim 4, wherein the impedance means is located on at least two of a first surface and a second surface that are inner layers of surfaces in a thickness direction of the substrate for the medical device, and is provided such that at least part of the impedance means overlap along the thickness direction of the substrate for the medical device.

6. The medical device according to claim 2, wherein the impedance means includes a dielectric sheet.

7. The substrate for the medical device according to claim 1, further comprising:
a plurality of the isolated circuits; and an impedance means for connecting two of the plurality of isolated circuits.

8. The substrate for the medical device according to claim 1, comprising a conductor provided in the ground-side circuit and fixed in the medical device while being conductively connected to a ground-side circuit or a grounding unit provided in the medical device and yet outside the substrate for the medical device.

9. The medical device according to claim 1, wherein the isolated circuit is placed at a position where stray capacitance occurs between the patient circuit and the ground-side circuit.

10. The medical device according to claim 1, wherein the patient circuit and the ground-side circuit are arranged on a same layer in a thickness direction of the substrate.

11. The substrate for the medical device according to claim 1, wherein the isolated circuit and the first and second impedance circuits are located on at least one of a first surface and a second surface that are inner layers of surfaces in a thickness direction of the substrate for the medical device.

12. The substrate for the medical device according to claim 1, further comprising:
a plurality of the isolated circuits; and
an impedance circuit configured to provide a predetermined impedance for connecting two of the plurality of isolated circuits.

13. The substrate for the medical device according to claim 1, wherein each of the first impedance circuit and the second impedance circuit is formed of a chip-type surface mount electronic component.

14. The substrate for the medical device according to claim 13, wherein the at least one of the first impedance circuit and the second impedance circuit is located on at least two of a first surface and a second surface that are inner layers of surfaces in a thickness direction of the substrate for the medical device, and is provided such that at least part of the first and second impedance circuits overlap in the thickness direction of the substrate for the medical device.

15. The medical device according to claim 1, wherein at least one of the first impedance circuit and the second impedance circuit includes a dielectric sheet.

16. The substrate for the medical device according to claim 1, wherein the first and second impedance circuits are arranged to overlap the insulating layer, the first impedance circuit connects the patient circuit to the isolated circuit across the insulating layer, and the second impedance circuit connects the ground-side circuit to the isolated circuit across the insulating layer.

17. The substrate for the medical device according to claim 1, wherein the patient circuit and the ground-side circuit include a plurality of surface-mount type electronic components.

18. The substrate for the medical device according to claim 1, wherein the first and second impedance circuits include at least one of a capacitor, a coil, and a resistance.

19. The substrate for the medical device according to claim 1, wherein the first impedance circuit and the second impedance circuit are arranged on a same layer in a thickness direction of the substrate.

20. A medical device, a portion of which is brought into contact with or inserted into a subject,
the medical device comprising a substrate for the medical device,
wherein the substrate for the medical device includes
a patient circuit that is conductively connected to the portion of the medical device that is configured to be brought into contact with or inserted into the subject,
a ground-side circuit that is a circuit configured to perform at least one of transmission of a signal, reception of a signal, and supply of electric power on the patient circuit, the ground-side circuit being grounded by a protective ground to ensure safety of a manipulator of the medical device
an insulating layer provided between the patient circuit and the ground-side circuit and providing insulation between the patient circuit and the ground-side circuit,
an isolated circuit provided apart from the patient circuit and the ground-side circuit on the insulating layer and having a different reference potential from the patient circuit and the ground-side circuit, and
a first impedance circuit that connects the patient circuit to the isolated circuit, and a second impedance circuit that connects the around-side circuit to the isolated circuit, at least one of the first and second impedance circuits being formed of a chip-type surface mount electronic component.

21. The medical device according to claim 20, comprising:
a tip device including a circuit unit conductively connected to the patient circuit and being configured to be brought into contact with or inserted into the subject; and
a control device including the substrate for the medical device and being configured to control operation of the tip device.

22. The medical device according to claim 20, further comprising an electrically conductive fixing means for fixing the substrate for the medical device in the medical device,
wherein the ground-side circuit is grounded via the fixing means.

23. The medical device according to claim 20, comprising:
a tip circuit conductively connected to the patient circuit and being configured to be brought into contact with or inserted into the subject; and
a control processing circuit including the substrate for the medical device and being configured to control operation of the tip circuit.

24. The medical device according to claim 20, further comprising an electrically conductive fastener for fixing the substrate for the medical device in the medical device,
wherein the ground-side circuit is grounded via the electrically conductive fastener.

* * * * *